(12) United States Patent
Bierl et al.

(10) Patent No.: US 9,151,737 B2
(45) Date of Patent: Oct. 6, 2015

(54) METHOD AND DEVICE FOR CALIBRATING A SENSOR

(75) Inventors: Rudolf Bierl, Regensburg (DE);
Stephan Heinrich, Pfeffenhausen (DE);
Andreas Wildgen, Nittendorf (DE)

(73) Assignee: Continental Automotive GmbH,
Hannover (DE)

( * ) Notice: Subject to any disclaimer, the term of this patent is extended or adjusted under 35 U.S.C. 154(b) by 938 days.

(21) Appl. No.: 13/140,266

(22) PCT Filed: Dec. 15, 2009

(86) PCT No.: PCT/EP2009/067200
§ 371 (c)(1),
(2), (4) Date: Jun. 30, 2011

(87) PCT Pub. No.: WO2010/076196
PCT Pub. Date: Jul. 8, 2010

(65) Prior Publication Data
US 2011/0289999 A1    Dec. 1, 2011

(30) Foreign Application Priority Data

Dec. 16, 2008 (DE) .......................... 10 2008 062 550

(51) Int. Cl.
*G01N 33/00* (2006.01)
*F02D 41/00* (2006.01)
*F02D 41/14* (2006.01)
*F02D 41/24* (2006.01)

(52) U.S. Cl.
CPC ........ *G01N 33/0006* (2013.01); *F02D 41/0045* (2013.01); *F02D 41/1456* (2013.01); *F02D 41/2474* (2013.01)

(58) Field of Classification Search
USPC ......................................... 73/1.06, 1.03, 1.07
See application file for complete search history.

(56) References Cited

U.S. PATENT DOCUMENTS

| 4,145,272 | A  | * | 3/1979  | Nakamura et al. ............ 204/412 |
| 5,186,153 | A  |   | 2/1993  | Steinbrenner et al. |
| 6,230,484 | B1 |   | 5/2001  | Kerns |
| 6,237,575 | B1 |   | 5/2001  | Lambert et al. |
| 6,499,476 | B1 | * | 12/2002 | Reddy ............................ 123/704 |
| 7,774,128 | B2 | * | 8/2010  | Kim .............................. 701/109 |
| 2003/0106544 | A1 | | 6/2003  | Davis et al. |

FOREIGN PATENT DOCUMENTS

| DE | 40 25 544 A1  | 10/1991 |
| DE | 4025544       | 10/1991 |
| EP | 1 074 728 A2  | 2/2001  |
| EP | 1074728       | 2/2001  |
| JP | 2003-148196 A | 5/2003  |
| JP | 2003148196    | 5/2003  |
| JP | 2004-44600 A  | 2/2004  |
| JP | 2004044600    | 2/2004  |

* cited by examiner

*Primary Examiner* — Paul West
(74) *Attorney, Agent, or Firm* — Cozen O'Connor

(57) ABSTRACT

A tank ventilation system having an intake tract, the tank ventilation system including a hydrocarbon reservoir, a sensor, and a valve. The valve and the sensor are arranged in a fluid line that couples the hydrocarbon reservoir to the intake tract. The sensor captures a hydrocarbon concentration of a fluid in the fluid line. A captured value of the hydrocarbon concentration is measured using the sensor. When the open valve, a mass flow of the fluid flowing through the fluid line into the intake tract is captured or determined. An air/fuel ratio of an air/fuel mixture fed to the internal combustion engine is determined. An estimated value of the hydrocarbon concentration in the fluid line is determined according to the mass flow of the fluid and the air/fuel ratio. The sensor is calibrated according to the captured value of the hydrocarbon concentration and the estimated value of the hydrocarbon concentration.

5 Claims, 3 Drawing Sheets

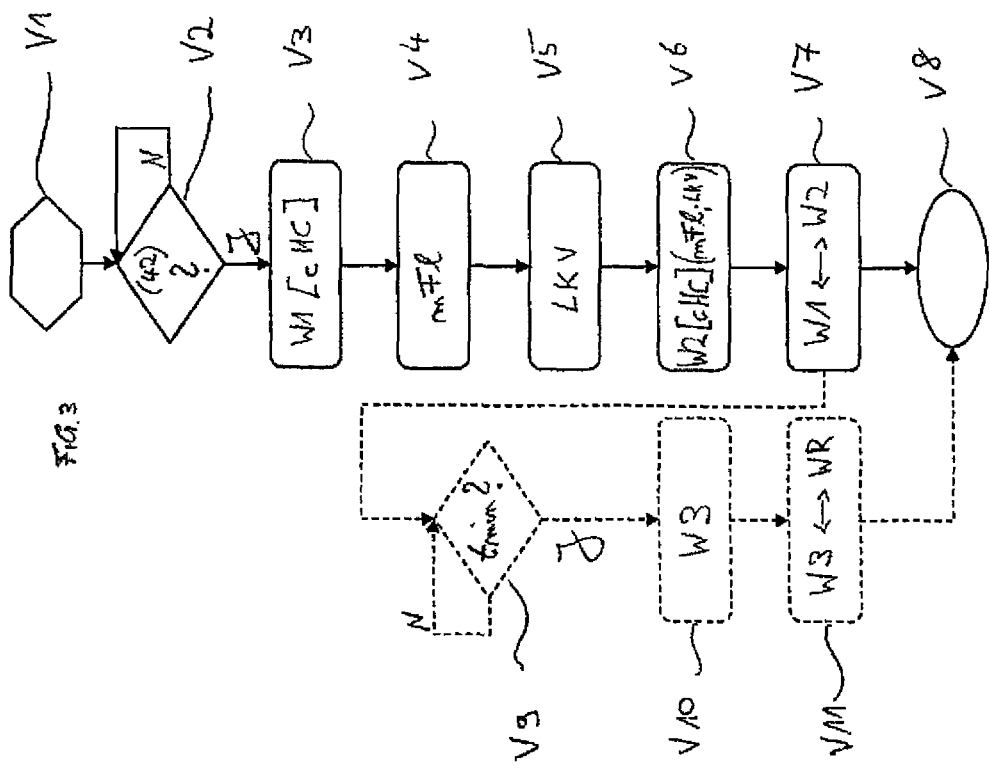
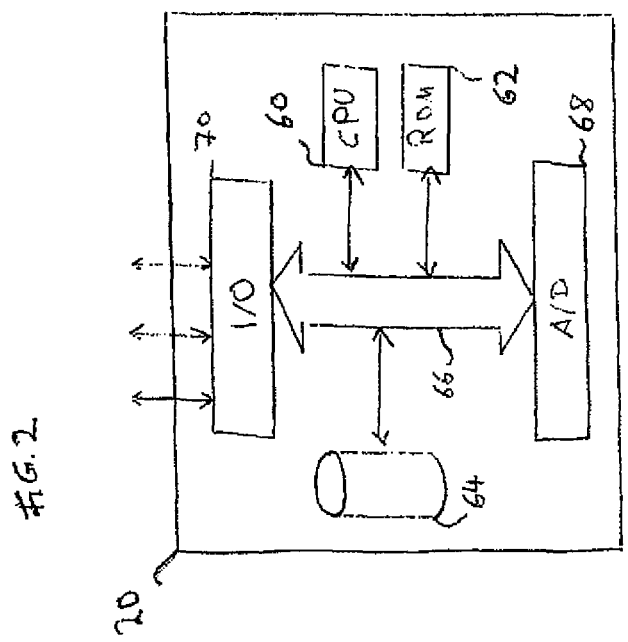

FIG. 4

$$LKV \cdot K = \frac{m_L + m_{Fl}(1 - {}_cHC)}{m_K + m_{Fl} \cdot {}_cHC} \quad G1$$

METHOD AND DEVICE FOR CALIBRATING A SENSOR

PRIORITY CLAIM

This is a U.S. national stage of Application No. PCT/EP2009/067200, filed on Dec. 15, 2009, which claims priority to German Application No: 10 2008 062 550.7, filed: Dec. 16, 2008, the contents of which are incorporated herein by reference.

BACKGROUND OF THE INVENTION

1. Field of the Invention

The invention relates to a method and a device for calibrating a sensor. During operation of an internal combustion engine, a large portion of the emitted pollutants are due to exhaust gas produced as a result of combustion. Other sources are also responsible for emitting pollutants. These sources may include, for example, evaporative emissions from a fuel tank of the internal combustion engine.

2. Related Art

Fuels such as premium grade gasoline stored in the fuel tank contain a number of highly volatile hydrocarbons. These include, for example, methane, butane and propane. In order to protect the fuel tank from mechanical damage in the event of a change in the volume of the fuel and to allow pressure equalization between the fuel tank and the ambient air, the fuel tank can be coupled to the ambient air via a line. The highly volatile hydrocarbons can be released from the fuel, particularly at high outside temperatures due to irradiation by the sun, or vibration of the fuel tank during driving, and can leave the fuel tank via the line as gaseous components.

SUMMARY OF THE INVENTION

One embodiment of the invention is based on providing a method and a device with which a sensor of a tank ventilation system designed to detect a concentration of hydrocarbons of a fluid can be calibrated in a simple and reliable manner.

According to one embodiment of the invention is a method and a corresponding device for calibrating a sensor of a tank ventilation system. The tank ventilation system is arranged in an internal combustion engine which has an intake section. The tank ventilation system comprises a hydrocarbons storage and a valve, the valve and the sensor being arranged in a fluid line. The fluid line couples the hydrocarbons storage device to the intake section. The sensor is designed to detect a concentration of hydrocarbons in a fluid in the fluid line. When the valve is open, a detected value for the concentration of hydrocarbons is detected by the sensor. A mass flow of the fluid flowing through the fluid line into the intake section is detected or determined when the valve is open. The mass flow can influence the concentration of hydrocarbons in an air/fuel mixture which is fed in a metered manner to the internal combustion engine for combustion purposes. An air/fuel ratio is determined from the air/fuel mixture when the valve is open. In particular, the detected value for the concentration of hydrocarbons, the mass flow and the air/fuel ratio are detected or determined at approximately the same time in such a way that the actual concentration of hydrocarbons is largely unchanged during the detection or determination process. An estimated value for the concentration of hydrocarbons in the fluid line is determined as a function of the mass flow of the fluid and the air/fuel ratio. The sensor is calibrated as a function of the detected value of the concentration of hydrocarbons and the estimated value for the concentration of hydrocarbons. This allows a degree of long-term stability of measurement signals from the sensor on account of it being possible for the sensor to be calibrated in a reliable manner.

According to one embodiment, the air/fuel ratio is determined as a function of a measurement signal from an exhaust gas probe in an exhaust gas section of the internal combustion engine. The exhaust gas probe may be, for example, a lambda probe. This may make the installation of additional measurement devices obsolete.

In one embodiment, a check is made to determine whether the valve has been open at least for a prespecified time period, and if the valve has been open at least for the prespecified time period, a further detected value for the concentration of hydrocarbons is detected by the sensor. The sensor is calibrated as a function of the further detected value for the concentration of hydrocarbons and a prespecified reference value. This allows reliable calibration of the sensor independently of another measurement device.

According to one embodiment of the invention a corresponding device for calibrating a sensor of a tank ventilation system. The tank ventilation system is arranged in an internal combustion engine which has an intake section. The tank ventilation system comprises a hydrocarbons storage device and a valve, the valve and the sensor being arranged in a fluid line. The fluid line couples the hydrocarbons storage device to the intake section. The sensor is designed to detect a concentration of hydrocarbons in a fluid in the fluid line. A check is made to determine whether the valve has been open at least for a prespecified time period. If the valve has been open at least for the prespecified time period, a further detected value for the concentration of hydrocarbons is detected by the sensor. The sensor is calibrated as a function of the further detected value for the concentration of hydrocarbons and a prespecified reference value.

In one embodiment, the prespecified reference value is characteristic of a minimum concentration of hydrocarbons in the fluid line. This allows simple and reliable calibration of the sensor to a minimum value.

BRIEF DESCRIPTION OF DRAWINGS

Exemplary embodiments of the invention are explained in greater detail below with reference to the schematic drawings, in which:

FIG. 2 is a control device;

FIG. 3 is a flowchart; and

FIG. 4 is an equation.

Elements of similar design or function are identified by the same reference symbols throughout the figures.

DETAILED DESCRIPTION OF THE PREFERRED EMBODIMENTS

Figure 1:
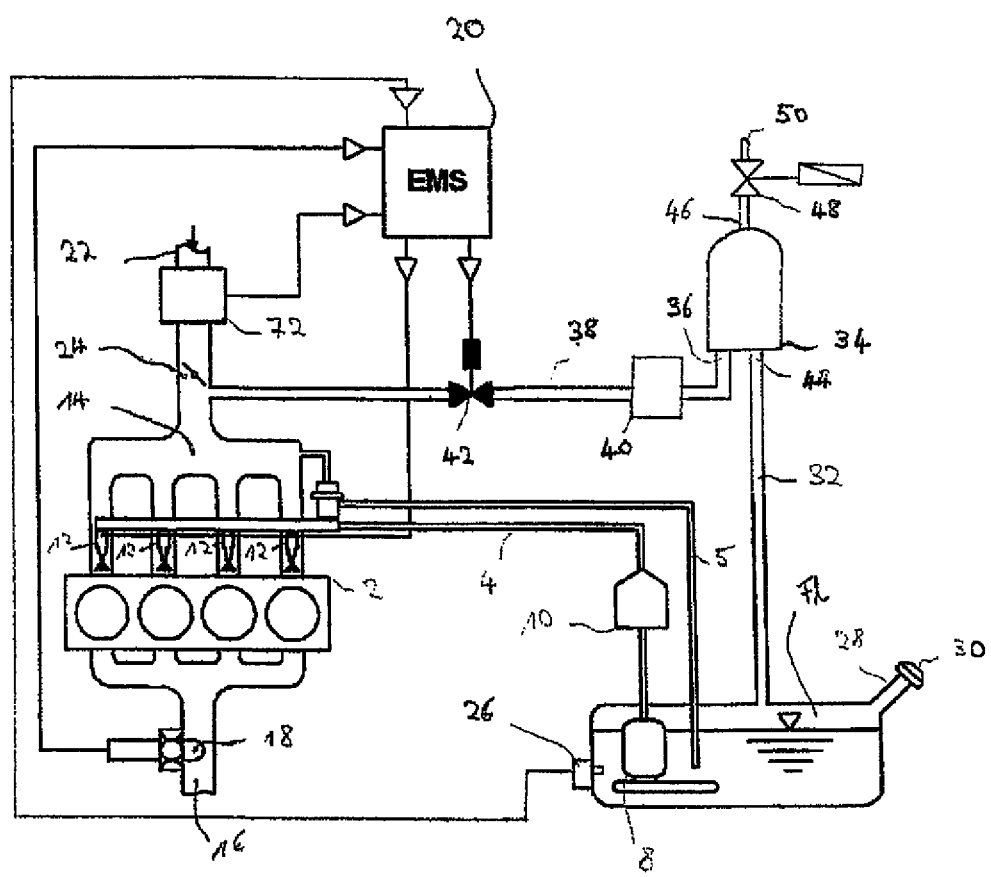
FIG. 1 is an internal combustion engine having a tank ventilation system.

FIG. 1 shows an internal combustion engine with an engine block 2 coupled hydraulically to a tank 6 by a fuel supply line 4 and a return line 5. The tank 6 may be, for example, a fuel tank which can be filled with fuel. A fuel delivery unit 8 is arranged in the tank 6, said fuel delivery unit passing fuel to injection valves 12, which are arranged on the engine block 2, via the fuel supply line 4 and a filter 10 which is arranged in the fuel supply line 4. The injection valves 12 feed the supplied fuel into the engine block 2 in a metered manner, and in said engine block said fuel is burnt together with air which is fed in a metered manner and in a prespecified ratio relative to the fuel by an intake section 14. Exhaust gases produced in the combustion process are conducted away from the engine block 2 by an exhaust gas section 16. A lambda probe 18, which is designed to generate a measurement signal which is representative of an air/fuel ratio LKV before combustion, is arranged in the exhaust gas section 16. The lambda probe 18 is electrically coupled to a control device 20 and is thus preferably part of a closed-loop lambda control system. The lambda probe 18 can also be called an exhaust gas probe. The control device 20 can be called a device for operating an internal combustion engine and can be in the form of an engine control unit. The air is fed to the intake system 14 via an air inlet 22 in which a throttle flap 24 is arranged.

A fuel sensor 26 is furthermore arranged in the tank 6. The fuel sensor 26 may be, for example, a "flex-fuel sensor" by which the composition of the fuel can be determined. Highly volatile hydrocarbons may evaporate from the fuel, particularly at high ambient temperatures. This gives rise to an air/fuel mixture enriched with hydrocarbons in the tank 6, said mixture being called fluid Fl in the text which follows.

The tank 6 has a filler neck 28, at the end of which it is closed off hermetically from the outside by a tank cap 30. While the internal combustion engine is in operation, there may be a reduction in the volume of the fuel stored in the tank 6, for example owing to extraction of fuel by the fuel delivery unit 8. It is also possible, for example, to increase the volume of fuel in the tank 6, for example owing to temperature-induced expansion of the fuel at high outside temperatures and relatively long downtimes of the internal combustion engine. In order to counteract damage to the tank 6 in an effective manner, the tank 6 is coupled to a ventilation line 32 to allow pressure equalization between the tank 6 and the ambient air if there is a change in the volume of the tank contents. If there are changes in the volume of the tank contents, the fluid Fl which is enriched with hydrocarbons can enter the ventilation line 32. It is also possible, for example, for fuel to enter the ventilation line 32, for example owing to vibration of a vehicle in which the internal combustion engine with the tank 6 is arranged. In this case, the proportion of hydrocarbons in the fluid Fl is particularly high.

The internal combustion engine has a hydrocarbons storage device 34 for filtering the hydrocarbons contained in the fluid Fl. The hydrocarbons storage device 34 can be in the form of an activated carbon filter and is designed to absorb and store hydrocarbons. The hydrocarbons storage device 34 has three connections. A first connection 36 is coupled to a purge line 38 which can also be called a fluid line in general and is coupled to the intake section 14 via a sensor 40 and a valve 42. The hydrocarbons storage device 34 is coupled to the tank 6 via a second connection 44 and the ventilation line 32. A third connection 46 couples the hydrocarbons storage device 34 to a purge air inlet 50 via a purge valve 48.

In one embodiment, the valve 42 is in the form of an analog valve 42. This allows open positions of the valve 42 to be prespecified in a stepless manner. In particular, for example in contrast to a digital valve, pulsations in the purge line 38 can be effectively prevented.

The absorption capacity of the hydrocarbons storage device 34 in respect of hydrocarbons is limited. If the hydrocarbons storage device 34 reaches saturation, it is purged. To this end, the purge valve 48 and valve 42 are opened, with the result that ambient air enters the hydrocarbons storage device 34 via the purge air inlet 50 and the purge valve 48, said ambient air absorbing the hydrocarbons stored in the hydrocarbons storage device 34 and feeding them in a metered manner to the intake section 14 of the internal combustion engine via the sensor 40 and the purge line 38. To this end, the purge valve 48 and valve 42 can be controlled by the control device 20. The arrangement of the hydrocarbons storage device 34 with the fluid line 38, the sensor 40 and the valve 42 can also be called a tank ventilation system.

The air/fuel ratio LKV of the air/fuel mixture is prespecified in order to reduce pollutants from the internal combustion engine and also to optimize performance. The fluid Fl which is enriched with hydrocarbons from the hydrocarbons storage device 34 enters the intake system 14 via the valve 42, and said fluid can influence the composition of the air/fuel mixture in respect of the hydrocarbon content thereof in said intake system. In order to be able to prespecify the air/fuel ratio LKV in an accurate manner, a concentration of hydrocarbons cHC in the fluid Fl which is enriched with hydrocarbons is detected by the sensor 40. For a known concentration of hydrocarbons cHC in the fluid Fl, the supply of air from the air inlet 22 and of fuel can then be adapted accordingly. A mass flow mFl of the fluid Fl which is enriched with hydrocarbons can, for example, also be adapted by the valve 42, for example by the control device 20. In order to be able to also expect reliable measurement results from the sensor 40 over long periods of time, the sensor 40 can be calibrated, for example at regular intervals. The sensor 40 is preferably calibrated as a function of at least two measurement points. This allows the measurement signal to be corrected in respect of a shift in the zero point and a shift in a gradient of the measurement signal.

FIG. 2 shows the control device 20. The control device 20 comprises a processor 60, a program memory 62 and also a data storage means 64. The processor 60, the program memory 62 and also the data storage device 64 are coupled to one another via a system bus 66.

The control device 20 is designed to execute a program which is stored, for example, in the program memory 62. The sensor 40 can be calibrated by the program. The control device 20 can therefore likewise be called a device for calibrating the sensor 40. The data storage device 64 is designed to store data the measurement signals.

The system bus 66 is coupled to an analog/digital converter 68. The control device 20 is coupled to the fuel sensor 26 and to the sensor 40 for detecting the concentration of hydrocarbons cHC via the analog/digital converter 68. The received measurement signals can be stored, for example, in the data storage device 64 and processed by the processor 60. Furthermore, the control device 20 has an interface 70. For control purposes, the control device 20 is electrically coupled to the injection valves 12, the valve 42 and the purge valve 50 via the interface 70. Furthermore, the control device 20 is electrically coupled to the lambda probe 18 via the interface 70.

FIG. 3 shows a flowchart of the program which is executed, for example, by the control device 20. The program comprises eleven steps.

The program begins with a first step V1. Parameters can be initialized in the first step V1.

In a second step V2, a check is made to determine whether the valve 42 is open. If the valve is open, the program continues with a third step V3. If the valve 42 is closed, the program continues with the second step V2.

A detected value W1 of the concentration of hydrocarbons cHC is detected by the sensor 40 in the third step V3.

The mass flow mFl of the fluid Fl flowing through the fluid line 38 into the intake section 14 is detected or determined in the fourth step V4. The mass flow mFl can be detected, for example, by a fluid mass sensor. However, it is also possible for the sensor 40 to be designed to also detect the mass flow mFl of the fluid Fl, in addition to the concentration of hydrocarbons cHC. If a suitable sensor is not arranged in the fluid line 38, the mass flow mFl can be determined as a function of a pressure difference between the fluid line 38 and the intake section 14 of the internal combustion engine, taking further account of a diameter of the fluid line 38. A temperature can also be taken into consideration in order to determine the mass flow mFl of the fluid Fl. The fluid Fl enriched with hydrocarbons can flow from the fluid line 38 into the intake section 14 on account of the pressure difference.

An air/fuel ratio LKV of an air/fuel mixture is determined in a fifth step V5. The air/fuel mixture is designed to be burnt in the internal combustion engine and is composed of the air which has been drawn in through the air inlet 22, the fuel which is fed in a metered manner by the injection valves 12, and the fluid Fl which is enriched with carbon. The air/fuel ratio LKV can be determined, for example by the lambda probe 18, in the exhaust gas section 16 after the air/fuel mixture is burnt.

An estimated value W2 for the concentration of hydrocarbons cHC is determined as a function of the mass flow mFl of the fluid Fl and the air/fuel ratio LKV in a sixth step V6. An assignment prespecification for determining the concentration of hydrocarbons cHC is given by an equation G1 in FIG. 4. The right-hand side of the equation is composed of the air/fuel ratio LKV and a constant k which may be a stoichiometric factor. The left-hand side of the equation G1 is composed, in addition to the concentration of hydrocarbons cHC and the mass flow mFl of the fluid Fl, of a mass flow of injected fuel mK and a mass flow of metered air mL. The mass flow of metered air mL is fed in a metered manner into the intake section 14 via the air inlet 22 and can be determined, for example, by an air mass flow sensor 72.

The sensor 40 is calibrated in a seventh step V7. In this context, assignment of the measurement signal from the sensor 40 to detected values of the concentration of hydrocarbons cHC is adapted. This can be done, for example, by determining a correction value which is then accordingly used to adapt the detected values during later operation. Furthermore, a characteristic diagram, which is provided for assigning the measurement signals from the sensor 40 to detected values of the concentration of hydrocarbons cHC, can also be adapted.

A relationship between the detected value W1 and the estimated value W2 is determined to this end. For this purpose, a factor with which the detected value W1 can be mapped onto the estimated value W2 can be determined. However, it is also possible for a difference between the detected value W1 and the estimated value W2 or any other desired assignment prespecification between the detected value W1 and the estimated value W2 to be determined. The program can be terminated after the seventh step V7 with an eighth step V8. However, in a preferred embodiment, the program continues with a ninth step V9.

In the ninth step V9, a check is made to determine whether the valve 42 has been opened at least for a prespecified time period tmin. If this is not the case, the program continues with the ninth step V9. If the valve 42 has been open at least for the prespecified time period tmin, the program continues with a tenth step V10.

A further detected value W3 for the concentration of hydrocarbons cHC is detected in the tenth step V10.

The sensor 40 is calibrated as a function of the further detected value W3 and a prespecified reference value WR in the eleventh step V11. In a preferred embodiment, the prespecified reference value WR is characteristic of a minimum concentration of hydrocarbons cHC in the fluid line 38. If the prespecified time period tmin is selected to be very long, it can be assumed, for example, that the fluid Fl flowing through the fluid line 38 no longer contains any hydrocarbons. In this case, the prespecified reference value WR may be zero. After the eleventh step V11 is executed, the program is terminated with the eighth step V8.

Additional execution of steps V9 to V11 has the advantage that the sensor 40 can be calibrated both in respect of its zero point and in respect of the gradient of the measurement signal. This allows both a drift in the zero point and a change in the gradient of the measurement signal from the sensor 40 to be taken into consideration.

Steps V3 to V5 are executed at approximately the same time in such a way that the actual concentration of hydrocarbons cHC is largely unchanged when implementing steps V3 to V5.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for calibrating a tank ventilation system sensor configured to detect a concentration of hydrocarbons in a fluid in a fluid line for an internal combustion engine with an intake section having a hydrocarbon storage device and a valve, the valve and the sensor arranged in the fluid line configured to couple the hydrocarbon storage device to the intake section, the method comprising:
    detecting a value for the concentration of hydrocarbons by the sensor when the valve is open;
    at least one of detecting and determining a mass flow of the fluid flowing through the fluid line into the intake section when the valve is open;
    determining an air/fuel ratio of an air/fuel mixture supplied to the internal combustion engine for combustion purposes when the valve is open;
    determining an estimated value for the concentration of hydrocarbons in the fluid line as a function of the mass flow of the fluid and the air/fuel ratio; and
    calibrating the sensor as a function of the detected value for the concentration of hydrocarbons and the estimated value for the concentration of hydrocarbons.

2. The method as claimed in claim 1, wherein the air/fuel ratio is determined as a function of a measurement signal from an exhaust gas probe in an exhaust gas section of the internal combustion engine.

3. The method as claimed in claim 1, further comprising:
    checking to determine whether the valve has been open at least for a prespecified time period (tmin), and if the valve has been open at least for the prespecified time period:
    detecting a further detected value for the concentration of hydrocarbons by the sensor; and
        calibrating the sensor as a function of the further detected value for the concentration of hydrocarbons and a prespecified reference value.

4. The method as claimed in claim 3, wherein the prespecified reference value is characteristic of a minimum concentration of hydrocarbons in the fluid line.

5. A device for calibrating a sensor configured to detect a concentration of hydrocarbons in a fluid of a tank ventilation system arranged in an internal combustion engine with an intake section, a hydrocarbon storage device, and a valve, the valve and the sensor being arranged in the fluid line coupling the hydrocarbon storage device to the intake section, the sensor configured to:
 detect a detected value for the concentration of hydrocarbons by the sensor when the valve is open;
  one of detect and determine a mass flow of the fluid flowing through the fluid line into the intake section when the valve is open;
 determine the air/fuel ratio from an air/fuel mixture which is supplied to the internal combustion engine for combustion purposes when the valve is open;
 determine an estimated value for the concentration of hydrocarbons in the fluid line as a function of the mass flow of the fluid and the air/fuel ratio; and
 calibrate the sensor as a function of the detected value for the concentration of hydrocarbons and the estimated value for the concentration of hydrocarbons.

* * * * *